US012580046B2

(12) United States Patent
Browning et al.

(10) Patent No.: US 12,580,046 B2
(45) Date of Patent: ***Mar. 17, 2026

(54) COMPUTER METHOD AND SYSTEM OF IDENTIFYING GENOMIC MUTATIONS USING GRAPH-BASED LOCAL ASSEMBLY

(71) Applicant: Seven Bridges Genomics, Inc., Cambridge, MA (US)

(72) Inventors: John Browning, Woburn, MA (US); Deniz Kural, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 1067 days.

This patent is subject to a terminal disclaimer.

(21) Appl. No.: 17/651,396

(22) Filed: Feb. 16, 2022

(65) Prior Publication Data

US 2022/0172800 A1 Jun. 2, 2022

Related U.S. Application Data

(63) Continuation of application No. 15/669,141, filed on Aug. 4, 2017, now Pat. No. 11,289,177.

(60) Provisional application No. 62/372,020, filed on Aug. 8, 2016.

(51) Int. Cl.
| | |
|---|---|
| *G16B 30/20* | (2019.01) |
| *G16B 20/00* | (2019.01) |
| *G16B 20/20* | (2019.01) |
| *G16B 30/00* | (2019.01) |
| *G16B 30/10* | (2019.01) |
| *G16B 45/00* | (2019.01) |

(52) U.S. Cl.
CPC ............. *G16B 30/20* (2019.02); *G16B 20/00* (2019.02); *G16B 20/20* (2019.02); *G16B 30/00* (2019.02); *G16B 30/10* (2019.02); *G16B 45/00* (2019.02)

(58) Field of Classification Search
CPC ........ G16B 30/20; G16B 20/00; G16B 20/20; G16B 30/00; G16B 30/10; G16B 45/00
See application file for complete search history.

(56) References Cited

U.S. PATENT DOCUMENTS

| | | | |
|---|---|---|---|
| 5,511,158 | A | 4/1996 | Sims |
| 5,701,256 | A | 12/1997 | Marr et al. |
| 6,054,278 | A | 4/2000 | Dodge et al. |
| 6,223,128 | B1 | 4/2001 | Allex et al. |
| 7,577,554 | B2 | 8/2009 | Lystad et al. |
| 7,580,918 | B2 | 8/2009 | Chang et al. |
| 7,809,509 | B2 | 10/2010 | Milosavljevic |
| 7,885,840 | B2 | 2/2011 | Sadiq et al. |
| 7,917,302 | B2 | 3/2011 | Rognes |
| 8,209,130 | B1 | 6/2012 | Kennedy et al. |
| 8,340,914 | B2 | 12/2012 | Gatewood et al. |
| 8,370,079 | B2 | 2/2013 | Sorenson |
| 8,639,847 | B2 | 1/2014 | Blaszczak et al. |
| 9,063,914 | B2 | 6/2015 | Kural et al. |
| 9,092,402 | B2 | 7/2015 | Kural et al. |
| 9,116,866 | B2 | 8/2015 | Kural |
| 9,390,226 | B2 | 7/2016 | Kural |
| 9,817,944 | B2 | 11/2017 | Kural |
| 11,289,177 | B2 | 3/2022 | Browning et al. |
| 2004/0023209 | A1 | 2/2004 | Jonasson |
| 2005/0089906 | A1 | 4/2005 | Furuta et al. |
| 2006/0292611 | A1 | 12/2006 | Berka et al. |
| 2007/0166707 | A1 | 7/2007 | Schadt et al. |
| 2008/0077607 | A1 | 3/2008 | Gatewood et al. |
| 2008/0294403 | A1 | 11/2008 | Zhu et al. |
| 2009/0119313 | A1 | 5/2009 | Pearce |
| 2009/0164135 | A1 | 6/2009 | Brodzik et al. |
| 2009/0300781 | A1 | 12/2009 | Bancroft et al. |
| 2010/0041048 | A1 | 2/2010 | Diehi et al. |
| 2010/0169026 | A1 | 7/2010 | Sorenson et al. |

(Continued)

FOREIGN PATENT DOCUMENTS

| | | |
|---|---|---|
| WO | WO2012096579 A3 | 7/2012 |
| WO | WO2012098515 A1 | 7/2012 |

(Continued)

OTHER PUBLICATIONS

Allam, A., Kalnis, P. and Solovyev, V. Karect: accurate correction of substitution, insertion and deletion errors for next-generation sequencing data. Bioinformatics, 31(21), pp. 3421-3428. (Year: 2015).*

(Continued)

*Primary Examiner* — Olivia M. Wise

*Assistant Examiner* — Janna Nicole Schultzhaus

(74) *Attorney, Agent, or Firm* — Wolf, Greenfield & Sacks, P.C.

(57) ABSTRACT

Computer-implemented methods and systems for performing a local assembly of a genomic region of interest include the de novo or assisted creation of a directed graph, such as a directed acyclic graph (DAG), from a plurality of obtained nucleotide sequence reads. First and second sequence reads are aligned to each other to define at least one node of the DAG. Successive alignments of the remaining sequence reads to the then-defined DAG are performed to extend nodes and/or add nodes to the DAG. Graph-aware alignment techniques that produce alignment scores or indicators are employed in defining the nodes of the DAG from the sequence reads. The created DAG represents and describes in detail the genomic region of interest and can be used to perform variant calls.

31 Claims, 7 Drawing Sheets

Specification includes a Sequence Listing.

(56)        References Cited

U.S. PATENT DOCUMENTS

| 2011/0004413 A1 | 1/2011 | Camevaii et al. |
| 2011/0098193 A1 | 4/2011 | Kingsmore et al. |
| 2012/0041727 A1 | 2/2012 | Mishra et al. |
| 2012/0045771 A1 | 2/2012 | Beier et al. |
| 2012/0239706 A1 | 9/2012 | Steinfadt |
| 2012/0330566 A1 | 12/2012 | Chaisson |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac |
| 2013/0289099 A1 | 10/2013 | Goff et al. |
| 2013/0311106 A1 | 11/2013 | White et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0323320 A1 | 10/2014 | Jia et al. |
| 2015/0056613 A1 | 2/2015 | Kural |
| 2015/0057946 A1 | 2/2015 | Kural |
| 2015/0094212 A1 | 4/2015 | Gottirnukkaia et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Sernenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |
| 2018/0039730 A1 | 2/2018 | Browning et al. |

FOREIGN PATENT DOCUMENTS

| WO | WO2012142531 A2 | 10/2012 |
| WO | WO2015027050 A1 | 2/2015 |
| WO | WO2015048753 A1 | 4/2015 |
| WO | WO2015058093 A1 | 4/2015 |
| WO | WO2015058095 A1 | 4/2015 |
| WO | WO2015058097 A1 | 4/2015 |
| WO | WO2015058120 A1 | 4/2015 |
| WO | WO2015061099 A1 | 4/2015 |
| WO | WO2015061103 A1 | 4/2015 |
| WO | WO2015105963 A1 | 7/2015 |
| WO | WO2015123269 A1 | 8/2015 |
| WO | WO2016141294 A1 | 9/2016 |
| WO | WO2016201215 A1 | 12/2016 |
| WO | WO2017120128 A1 | 7/2017 |
| WO | WO2017123864 A1 | 7/2017 |
| WO | WO2017147124 A1 | 8/2017 |

OTHER PUBLICATIONS

Durbin, R. et al., "Biological Sequence Analysis: Probabilistic Models of Proteins and Nucleic Acids," Cambridge University Press 1999.

Smith, T.F. et al., "Identification of Common Molecular Subsequences," J. Mol. Biol., 147(1):195-197, 1981.

Gotoh, O., "An Improved Algorithm for Matching Biological Sequences," J. Mol. Biol., 162(3):705-708, 1982.

Zerbino, D. R. et al., : Velvet: Algorithms for De Novo Short Read Assembly Using De Bruijn Graphs, Cold Spring Harbor Laboratory Press, 18:821-829, 2008.

Broad Institute Genome Analysis Toolkit (GATK): https://www.broadinstitute.org/gatk/guide/topic?name=methods.

Agarvval, 2013, SINNET: Social interaction Network Extractor from Text, Proc IJCNLP 33-36.

Aguiar, 2012, HapCompass: A fast cycle basis algorithm for accurate haplotype assembly of sequence data, J Comp D Biol 19(6):577-590.

Aguiar, 2013, Haplotype assembly in polyploid genomes and identical by descent shared tracts, Bioinformatics 29(13): i352-i360.

Airoldi, 2008, Mixed membership stochastic blockmodels, JMLR 9 1981-2014.

Albers, 2011, Dindel: Accurate indel calls from short-read data, Genome Research 21 :961-973.

Alioto et al., A comprehensive assessment of somatic mutation detection in cancer using whole-genome sequencing, Nature Communications, Dec. 9, 2015.

Altera, 2007, Implementation of the Smith-Waterman algorithm on reconfigurable supercomputing platform, White Paper per 1.0 (18 pages).

Altschul, 1986, Optimal Sequence Alignment Using Affine Gap Costs, Bull Math Biol 48(5/6):603-616.

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioninformatics 29 (10): 1250-1259.

Barbieri, 2013, Exome sequencing identifies recurrent SPOP, FOXA1 and MED12 mutations in prostate cancer, Nature Genetics 44:6 685-689.

Beerenwinkel, 2007, Conjunctive Bayesian Networks, Bernoulli 13(4), 893-909.

Berlin, 2014, Assembling large genomes with single-molecule sequencing and locality sensitive hashing, bioRxiv preprint (35 pages); retrieved from the internet on Jan. 29, 2015.

Bertrand, 2009, Genetic map refinement using a comparative genomic approach, J Comp Biol 16(10) 1475-1486.

Black, 2005, A simple answer for a splicing conundrum, PNAS 102:4927-8.

Boyer, 1977, A Fast String Searching Algorithm, Comm ACM 20(10):762-772.

Browning et al., Haplotype phasing: existing methods and new developments, 2011, vol. 12, Nature Reviews Genetics.

Caboche et al., Comparison of mapping algorithms used in high-throughput sequencing: application to Ion Torrent data, 2014, vol. 15, BMC Genomics.

Cartwright, DNA assembly with gaps (DAWG): simulating sequence evolution, 2005, pp. iii31-iii38, vol. 21, Oxford University Press.

Chang, 2005, The application of alternative splicing graphs in quantitative analysis of alternative splicing form from EST database, Int J Comp Appl Tech 22(1 ): 14.

Chin, 2013, Nonhybrid finished microbial genome assemblies from long-read SMRT sequencing data, Nat Meth 10 (6):563-569.

Chuang, 2001, Gene recognition based on DAG shortest paths, Bioinformatics 17(Suppl. 1):s56-s64.

Compeau, 2011, How to apply de Bruljn graphs to genome assembly, Nat 8iotect1 29(11):987-991.

Craig, 1990, Ordering of cosmid clones covering the Herpes simplex virus type 1 (HSV-I) genome: a test case for fingerprinting by hybridisation, Nucleic Acids Research 18:9 pp. 2653-2660.

Denoeud, 2004, Identification of polymorphic tandem repeats by direct comparison of genome sequence from different bacterial strains: a web-based resource, BMC Bioinformatics 5:4 pp. 1-12.

Depristo, 2011, A framework for variation discovery and genotyping using next-generation DNA sequencing data, Nat Gen 43:491-498.

(56) References Cited

OTHER PUBLICATIONS

Duan et al., Optimizing de novo common wheat transcriptome assembly using short-read RNA-Seq data. (2012) pp. 1-12, vol. 13, BMC Genomics.

Dudley, 2009, A quick guide for developing effective bioinformatics programming skills, PLoS Comput Biol 5(12): e1000589.

Durbin, 2014, Efficient haplotype matching and storage using the positional Burrows-Wheeler transform (PBWT), Bioinformatics 30(9):1266-1272.

Endelman, 2011, New algorithm improves fine structure of the barley consensus SNP map, Bl'v1C Genomics 12(1):407 (and whole document).

Exam Report issued in EP14803268.3.

Examination Report issued in Sg 11201601124Y.

Extended European Search Report issued in EP 14837955.5.

Extended European Search Report issued in EP 14847490.1.

Extended European Search Report issued in EP 14854801.9.

Farrar, 2007, Striped Smith-Waterman speeds database searches six times over other Si MD implementations, Bioinformatics 23(2):156-161.

Fitch, 1970, Distinguishing homologous from analogous proteins, Systematic Zoology 19:99-113.

Flicek, 2009, Sense from sequence reads: methods for alignment and assembly, Nat Meth Suppl 6(11s):s6-s12.

Florea, 2013, Genome-guided transcriptome assembly in the age of next-generation sequencing, IEEE/ACM Trans Comp Biol Bioinf 10(5):1234-1240.

Garber, 2011, Computational methods for transcriptome annotation and quantification using RNA-Seq, Nat Meth 8 (6):469-4 77.

Gerlinger, 2012, Intratumor Heterogeneity and Branched Evolution Revealed by Multiregion Sequencing, 366:10 883-892.

Golub, 1999, Molecular classification of cancer class discovery and class prediction by gene expression monitoring, Science 286, pp. 531-537.

Gotoh, 1982, An improved Algorithm for Matching Biological Sequences, J Mol Biol 162:705-708.

Gotoh, 1999, Multiple sequence alignment: algorithms and applications, Adv Biophys 36:159-206.

Grabherr, 2011, Full-length transcriptome assembly from RNA-Seq data without a reference genome, Nat Biotech 29 (7):644-654.

Grasso, 2004, Combining partial order alignment and progressive multiple sequence alignment increases alignment speed and scalability to very large alignment problems, Bioinformatics 20(10):1546-1556.

Guttman, 2010, Ab initio reconstruction of celi type-specific transcriptomes in mouse reveals the conserved multi-exonic structure of lincRNAs, Nat Biotech 28(5):503-510.

Guttman, 2010, Ab initio reconstruction of transcriptomes of pluripotent and lineage committed cells reveals gene structures of thousands of lincRNAs, NIH-PA Author Manuscript.

Haas, 2004, DAGchainer: a tool for mining segmental genome duplications and synteny, Bioinformatics 20 (18):3643-3646.

Harrow, 2012, GENCODE: The reference human genome annotation for The ENCODE Project, Genome Res 22: 1760-1774.

He, 2010, Optimal algorithms for haplotype assembly from whole-genome sequence data, Bioinformatics 26:i183-i190.

Heber, 2002, Splicing graphs and EST assembly problems, Bioinformatics 18 Suppl:181-188.

Hein, 1989, A new method that simultaneously aligns and reconstructs ancestral sequences for any number of homologous sequences when the phylogeny is given, Mol Biol Evol 6(6):649-668.

Hein, 1989, A tree reconstruction method that is economical in the number of pairwise comparisons used, Mol Biol Evol 6(6):649-668.

Horner, 2010, Improved variant discovery through local re-alignment of short-read next generation sequencing data using SRMA, Genome Biol 11 (1 0):R99.

Horspool, 1980, Practical Fast Searching in Strings, Software— Practice & Experience 10:501-506.

Huang, Chapter 3: Bio-Sequence Comparison and Alignment, ser. Curr Top Comp Mol Biol. Cambridge, Mass. The MIT Press, 2002.

Hutchinson, 2014, Allele-specific methylation occurs at genetic variants associated with complex diseases, PLoS One 9(6):e98464.

International Search Report and Written Opinion mailed Aug. 31, 2017, for International Application No. PCT/ US2017/018830 with International Filing Date Feb. 22, 2017, (11 pages), title Systems and Methods for Genotyping With Graph Reference.

International Search Report and Written Opinion mailed Mar. 31, 2015 for International Application No. PCT/ US2015/010604 (Client Ref SBG-010/01 WO) filed Jan. 8, 2015 (13 pages), title Systems and Methods for Use of Known Alleles in Read Mapping.

International Search Report and Written Opinion mailed Apr. 19, 2017 for international Patent Application No. PCT/ US2017/012015, (14 Pages), title Systems and Methods for Adaptive Local Alignment for Graph Genomes.

International Search Report and Written Opinion mailed Feb. 17, 2015, for International Patent Application No. PCT/US2014/061156, filed Oct. 17, 2014 (19 pages), title Methods and Systems for Genotyping Genetic Samples.

International Search Report and Written Opinion mailed Jan. 10, 2017, for International Patent Application No. PCT/US16/57324 with International Filing Date Oct. 17, 2016, (7 pages), title Biological Graph or Sequence Serialization.

International Search Report and Written Opinion mailed Mar. 19, 2015, for international Application No. PCT/ US2014/061162 with International Filing Date Oct. 17, 2014, (12 pages), title Methods and Systems for Identifying Disease-Induced Mutations.

International Search Report and Written Opinion mailed May 11, 2015, for International Patent Application No. PCT/ US2015/015375 with International Filing Date Feb. 11, 2015, (12 pages), title System and Methods for Analyzing Sequence Data.

International Search Report and Written Opinion mailed May 5, 2016, for International Patent Application No. PCT/ US2016/020899, with International Filing Date Mar. 4, 2016, (12 pages), title Systems and Methods for Genomic Pattern Analysis.

International Search Report and Written Opinion mailed on Apr. 7, 2017, for International Patent Application No. PCT/US2017/013329, filed Jan. 13, 2017, (9 pages), title Systems and Methods for Analyzing Circulating Tumor DNA.

International Search Report and Written Opinion mailed on Dec. 11, 2014, for International Patent Application No. PCT/US14/52065, filed Aug. 21, 2014, (18 pages), title, Methods and Systems for Aligning Sequences.

International Search Report and Written Opinion mailed on Dec. 30, 2014, for International Patent Application No. PCT/US14/58328, filed Sep. 30, 2014, (22 pages), title Methods and System for Detecting Sequence Variants.

International Search Report and Written Opinion mailed on Feb. 4, 2015, for International Patent Application No. PCT/US2014/061198, filed Oct. 17, 2014, (8 pages), title Methods and Systems for Aligning Sequences in the Presence of Repeating Elements.

International Search Report and Written Opinion mailed on Feb. 10, 2015, for International Patent Application No. PCT/US2014/060690, filed Oct. 15, 2014, PCT/US2014/060690 (11 pages), title Systems and Methods for Using Paired-End Data in Directed Acyclic Structure.

International Search Report and Written Opinion mailed on Feb. 4, 2015, for Patent Application No. PCT/ US2014/061158, filed Oct. 17, 2014, (11 pages), title Methods and Systems for Quantifying Sequence Alignment.

International Search Report and Written Opinion mailed on Jan. 27, 2015, for International Patent Application No. PCT/US2014/060680, filed October 215, 2014, (11 pages), title Systems and Methods for Transcriptome Analysis.

International Search Report and Written Opinion mailed Sep. 2, 2016, for International Patent Application No. PCT/US2016/033201 with International Filing Date May 19, 2016, (14 pages), title Systems and Methods for Haplotyping.

International Search Report and Written Opinion mailed Sep. 7, 2016, for International Application No. PCT/ US2016/036873 with International filing date Jun. 10, 2016, (8 pages), title Systems and Methods for Identifying Microorganisms.

Kano, 2010, Text mining meets workflow: linking U-Compare with Taverna, Bioinformatics 26(19):2486-7.

(56)        References Cited

OTHER PUBLICATIONS

Kehr, 2014, Genome alignment with graph data structures: a comparison, BMC Bioinformatics 15:99.

Kent, 2002, BLAT-The Blast-Like Alignment Tool, Genome Research 4:656-664.

Kim, 2005, ECgene: Genome-based EST clustering and gone modeling for alternative splicing, Genome Res 15:566-576 Kim, 2008, A Scaffold Analysis Tool Using Mate-Pair Information in Genome Sequencing, Journal of Biomedicine and Biotechnology 8(3):195-197.

Kim, 2013, TopHat2: accurate alignment of transcriptomes in the presence of insertions, deletions and gene fusions, Genome Biol 14(4):R36.

Koolen, 2008, Clinical and Molecular Delineation of the 17q21.31 Microdeletion Syndrome, J Med Gen 45(11):710-720.

Kumar, 2010, Comparing de novo assemblers for 454 transcriptome data, BMC Genornics 11 :571.

Kurtz, 2004, Versatile and open software for comparing large genomes, Genome Biol 5:R12.

Lam, 2008, Compressed indexing and local alignment of DNA, Bioinformatics 24(6):791-97.

Lang mead, 2009, Ultrafast and memory-efficient alignment of short DNA sequences to the human genome, Genome Biol 10:R25.

Larkin, 2007, Clustal Wand Clustal X version 2 0, Bioinformatics 23(21):2947-2948.

Lecca, 2015, Defining order and timing of mutations during cancer progression: the TO-DAG probabilistic graphical model, Frontiers in Genetics, vol. 6 Article 309 1-17.

Lee et al. Accurate read mapping using a graph-based human pan-genome. (May 2015) American Society of Human Genetics 64th Annual Meeting Platform Abstracts; Abstract 41.

Lee, 2002, Multiple sequence alignment using partial order graphs, Bioinformatics 18(3):452-464.

Lee, 2005, Bioinformatics analysis of alternative splicing, Brief Bioinf 6(1 ):23-33.

Lee, 2014, Accurate read mapping using a graph-based human pan-genome, ASHG 2014 Abstracts.

Legault, 2010, Learning Probalistic Splice Graphs from RNA-Seq data, pages.cs.wisc.eduHegauit/cs760_writeup.pdf; retrieved from the internet on Apr. 6, 2014.

Lcgault, 2013, Inference of alternative splicing from RNA-Scq data with probabilistic splicc graphs, Bioinformatics 29 (18):2300-2310.

Leipzig, 2004, The alternative splicing gallery (ASG): Bridging the gap between genome and transcriptome, Nuc Acids Res 23(13):3977-3983.

Li, 2009, Fast and accurate short read alignment with Burrows-Wheeler Transform. Bioinformatics 25:1754-60.

Li, 2010, A survey of sequence alignment algorithms for next-generation sequencing, Briefings in Bionformatics 11 (5) :4 73-483.

Lipman, 1985, Rapid and sensitive protein similarity searches, Science 227(4693): 1435-41.

Lucking, 2011, PICS-Ord: unlimited coding of ambiguous regions by pairwise identity and cost scores ordination, BMC Bio inf 12: 10.

Lupski, 2005, Genomic disorders: Molecular mechanisms for rearrangements and conveyed phenotypes, PLoS Genetics 1 (6):e49.

Ma, 2010, Multiple genome alignment based on longest path in directed acyclic graphs, Int J Bioinformatics 6 (4):366-683.

Mamoulis, 2004, Non-contiguous sequence pattern queries, in Advances in Database Technology—EDBT 2004: 9th.

International Conference on Extending Database Technology, Heraklion, Crete, Greece, Mar. 14-18, 2004, Proceedings (18 pages); retrieved from the internet on Jun. 3, 2016.

Marth et al., 1999—A general approach to single-nucleotide polymorphism discovery, pp. 452-456, vol. 23, Nature Genetics.

Mazrouee, 2014, FastHap: fast and accurate single individual haplotype reconstructions using fuzzy conflict graphs, Bioinformatics 30:i371-i378.

Mcsherry, 2001, Spectral partitioning of random graphs, Proc 42nd IEEE Symp Found Comp Sci 529-537.

Miller, 2010, Assembly Algorithms for Next-Generation Sequencing Data, Genomics 95(6):315-327.

Mount, 2001, Multiple Sequence Alignment, Bioinformatics, 2001, Cold Spring Harbor Laboratory Press, Cold Spring Harbor, New York, pp. 139-204.

Mourad, 2012, A hierarchical Bayesian network approach for linkage disequilibrium modeling and data-dimensionality reduction prior to genome-wide association studies, BMC Bioinformatics 12:16 1-20.

Myers, The Fragment Assembly String Graph, Bioinformatics, 2005, pp. ii79-ii85, vol. 21.

Nagarajan, 2013, Sequence assembly demystified, Nat Rev 14:157-167.

Nakao, 2005, Large-scale analysis of human alternative protein isoforms: pattern classification and correlation with subcellular localization signals, Nucl Ac Res 33(8):2355-2363.

Needleman, 1970, A general method applicable to the search for similarities in the amino acid sequence of two proteins, J Mol Biol 48(3):443-453.

Newman, 2013, Community detection and graph portioning, Europhys Lett 103(2):28003, arXiv:1305.4974v1.

Newman, 2014, An ultrasensitive method for quantitating circulating tumor DNA with broad patient coverage, Nature Medicine 20:5 1-11.

Olsson, 2015, Serial monitoring of circulating tumor DNA in patients with primary breast cancer for detection of occult metastatic disease, EMBO Molecular Medicine 7:8 1034-104 7.

Oshlack, 2010, From RNA-seq reads to differential expression results. Genome Bio 11 :220.

Parks, 2015, Detecting non-allelic homologous recombination from high-throughput sequencing data, Genome Biol 16:17.

Peixoto, 2014, Efficient Monte Caria and greedy heuristic for the inference of stochastic block models, Phys. Rev. E 89, 012804.

Pop et al., 2004, Comparative genome assembly, Briefings in Bioinformatics vol. 5, pp. 237-248.

Pruesse, 2012, SINA: Accurate high-throughput multiple sequence alignment of ribosomal RNA genes, Bioinformatics 28: 14 1823-1829.

Rajaram, 2013, Pearl millet [*Pennisetum glaucum* (L.) R Br.] consensus linkage map constructed using four RIL mapping populations and newly developed EST-SSRs, BMC Genomics 14(1 ): 159.

Raphael, 2004, A novel method for multiple alignment of sequences with repeated and shuffled elements, Genome Res 14:2336-2346.

Robertson, 2010, De novo assembly and analysis of RNA-seq data, Nat Meth 7(11 ):909.

Rodelsperger, 2008, Syntenator: Multiple gene order alignments with a gene-specific scoring function, Alg Mol Biol 3:14.

Rognes, 2000, Six-fold speed-up of Smith-Waterman sequence database searching using parallel processing on common microprocessors, Bioinformatics 16(8) :699-706.

Rogncs, 2001, ParAlign: a parallel sequencc alignment algorithm for rapid and sensitive database searches, Nucl Ac Res 29(7):1647-1652.

Rognes, 2011, Faster Smith-Waterman database searches with inter-sequence SIMD parailelisation, Bioinformatics 12:221.

Ronquist, 2012, MrBayes 3.2 efficient Bayesian phylogenetic inference and model choice across a large model space, Syst Biol 61 (3):539-42.

Saebo, 2005, PARALIGN: rapid and sensitive sequence similarity searches powered by parallel computing technology, Nucl Ac Res 33:W535-W539.

Sato, 2008, Directed acyclic graph kernels for structural RNA analysis, BMC (BioMed Central) Bioinformatics 9(318).

Schneeberger, 2009, Simultaneous alignment of short reads against multiple genomes, Genome Biol 10(9):R98.2-R98.12.

Schwikowski, 2002, Weighted sequence graphs: boosting iterated dynamic programming using locally suboptimal solutions, Disc Appl Mat 127:95-117.

Shao, 2006, Bioinformatic analysis of exon repetition, exon scrambling and trans-splicing in humans, Bioinformatics 22: 692-698.

Shendure et al. Next-generation DNA sequencing Nature Biotechnology vol. 26, pp. 1135-1145 (2008).

(56)                References Cited

OTHER PUBLICATIONS

Sievers, 2011, Fast, scalabie generation of high-quality protein multiple sequence alignments using Clustal Omeag, Mol Syst Biol 7:539.

Slater, 2005, Automated generation of heuristics for biological sequence comparison, BMC Bioinformatics 6:31.

Smith, 2012, Multiple insert size paired-end sequencing for deconvolution of complex transcriptions, RNA Bio 9(5) 596-609.

Sosa, 2012, Next-Generation Sequencing of Human Mitochondrial Reference Genomes Uncovers High Heteroplasmy Frequency, PLoS One 8(1O):e1002737.

Sturgeon, RCDA: a highly sensitive and specific alternatively spliced transcript assembly tool featuring upstream consecutive exon structures, Genomics, Dec. 2012, 100(6) 357-362.

Subramanian, 2008, DIAUGN-TX: greedy and progressive approaches for segment-based multiple sequence alignment, Alg Moi Biol 3(1):1-11.

Sudmant, 2015, An integrated map of structural variation in 2,504 human genomes, Nature 526 75-81.

Sun, 2006, Pairwise Comparison Between Genomic Sequences and Optical maps, dissertation, New York University (131 pages); retrieved from the internet on Jun. 3, 2016.

Szalkowski, 2012, Fast and robust multiple sequence alignment with phylogeny-aware gap placement, BMC (BioMed Central) Bioinformatics 13(129).

Szalkowski, 2013, Graph-based modeling of tandem repeats improves global multiple sequence alignment, Nucl Ac Res 41(17):e162.

Tarhio, 1993, Approximate Boyer-Moore String Matching, Siam J Comput 22(2):243-260.

Thomas, 2014, Community-wide effort aims to better represent variation in human reference genome, Genome Web (11 pages).

Trapnell, 2009, To pH at: discovering splice junctions with RNA-Seq, Bioinformatics 25: 1105-1111.

Trapnell, 2010, Transcript assembly and abundance estimation from RNA-Seq reveals thousands of new transcripts and switching among isoforms, Nat Biotech 28(5):511-515.

Trapnell, 2010, Transcript assembly and quantification by RNA-Seq reveals unannotated transcripts and isoform switching during cell differentiation, Nat Biotech 28(5):511-515.

Uchiyama et al., CGAT: a comparative genome analysis tool for visualizing alignments in the analysis of complex evolutionary changes between closely related genomes, 2006, e-pp. 1-17, vol. 7:472; BMC Bioinformatics.

Wang, 2009, RNA-Seq: a revolutionary tool for transcriptomics, Nat Rev Genet 10(1):57-63.

Written Opinion issued in SG 11201601124Y.

Written Opinion issued in SG 11201602903X.

Written Opinion issued in SG 11201603039P.

Written Opinion issued in SG 11201603044S.

Written Opinion issued in SG 112016055060.

Wu, 2010, Fast and SNP-tolerant detection of complex variants and splicing in short reads, Bioinformatics, 26 (7):873-881.

Xing, 2006, An expectation-maximization algorithm for probabilistic reconstructions of full-length isoforms from splice graphs, Nucleic Acids Research, 34:3150-3160.

Yang, 2013, Leveraging reads that span multiple single nucleotide polymorphisms for haplotype inference from sequencing data, Bioinformatics 29(18):2245-2252.

Yanovsky, 2008, Read mapping algorithms for single molecule sequencing data, Proc 8th Int Workshop Alg Bioinformatics 5251 :38-49.

Yu, 2010, The construction of a tetraploid cotton genome wide comprehensive reference map, Genomics 95:230-240.

Zeng, 2013, PyroHMMvar: a sensitive and accurate method to call short indels and SNPs for Ion Torrent and 454 data, Bioinformatics 29:22 2859-2868.

Zhang et al., Construction of a high-density genetic map for sesame based on large scale marker development by specific length amplified fragment (SLAF) sequencing. (2013) pp. 1-12, vol. 13, BMC Plant Biology.

Non-Final Office Action for U.S. Appl. No. 15/669,141, consisting of 40 pages. Mailed Apr. 5, 2019.

Final Office Action for U.S. Appl. No. 15/669,141, consisting of 12 pages. Mailed Nov. 15, 2019.

Non-Final Office Action for U.S. Appl. No. 15/669,141, consisting of 12 pages. Mailed Jun. 16, 2020.

Non-Final Office Action for U.S. Appl. No. 15/669,141, consisting of 11 pages. Mailed Jun. 25, 2021.

Notice of Allowance for U.S. Appl. No. 15/669,141, consisting of 9 pages. Mailed Nov. 22, 2021.

Supplemental Notice of Allowance for U.S. Appl. No. 15/669,141, consisting of 35 pages. Mailed Dec. 7, 2021.

Lee, 2003, Generating consensus sequences from partial order multiple sequence alignment graphs, Bioinformatics 19(8):999-1008.

* cited by examiner

R1    T A C T G G A C G C A T T C   (SEQ ID NO  3)

R2        C T G G A C G C A T T C A T   (SEQ ID NO  4)

G    T A C T G G A C G C A T T C A T    (SEQ ID NO  1)

R1    T A C T G G A C G C A T T C      (SEQ ID NO. 3)

R2        C T G G A C T C A T T C A T      (SEQ ID NO. 5)

G    T A C T G G A C  G  C A T T C A T    (SEQ ID NO. 1)

Deletion

SNP

Single Nucleotide
Insertion

Multiple Nucleotide
Insertion

Multiple Nucleotide
Variation

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: hypothetical nucleotide sequence read

<400> SEQUENCE: 1
tactggacgc attcat                                                            16

<210> SEQ ID NO 2
<211> LENGTH: 16
<212> TYPE: DNA
<213> ORGANISM: Artificial Sequence
<220> FEATURE:
<223> OTHER INFORMATION: hypothetical nucleotide sequence read

<400> SEQUENCE: 2
tactggactc attcat                                                            16

<210> SEQ ID NO 3
<211> LENGTH: 14
<212> TYPE: DNA
<213> ORGANISM: Artificial Sequence
<220> FEATURE:
<223> OTHER INFORMATION: hypothetical nucleotide sequence read

<400> SEQUENCE: 3
tactggacgc attc                                                              14

<210> SEQ ID NO 4
<211> LENGTH: 14
<212> TYPE: DNA
<213> ORGANISM: Artificial Sequence
<220> FEATURE:
<223> OTHER INFORMATION: hypothetical nucleotide sequence read

<400> SEQUENCE: 4
ctggacgcat tcat                                                              14

<210> SEQ ID NO 5
<211> LENGTH: 14
<212> TYPE: DNA
<213> ORGANISM: Artificial Sequence
<220> FEATURE:
<223> OTHER INFORMATION: hypothetical nucleotide sequence read

<400> SEQUENCE: 5
ctggactcat tcat                                                              14

COMPUTER METHOD AND SYSTEM OF IDENTIFYING GENOMIC MUTATIONS USING GRAPH-BASED LOCAL ASSEMBLY

RELATED APPLICATION

This application is a continuation of U.S. application Ser. No. 15/669,141, filed Aug. 4, 2017, which claims the benefit of U.S. Provisional Application No. 62/372,020, filed on Aug. 8, 2016. The entire teachings of the above application are incorporated herein by reference.

INCORPORATION BY REFERENCE OF MATERIAL IN ASCII TEXT FILE

This application incorporates by reference the Sequence Listing contained in the following ASCII text file:

a) File name: 5326.1000-002 Sequence Listing-3521543.txt; created Jan. 31, 2022, 1389 bytes in size.

BACKGROUND

Next-generation sequencing (NGS) is the current, dominant technique for characterizing DNA sequences. In NGS, long nucleotide polymers are sheared into small fragments that are then interrogated simultaneously by cycles of single-base-addition synthesis reactions. NGS produces millions of short sequence reads that mirror the sequence in the original molecules being studied. The short sequence reads produced by NGS must then be stitched together to form a consensus representation of the sequence of bases found in the original molecule. Aligning the short sequence reads to form the consensus representation is a complex process requiring execution of computationally demanding alignment algorithms. Additionally, the sequence reads produced by NGS, due to having relatively short lengths, often do not align well to reference sequences. There exists a need for improved methods of re-assembling sequence reads into a consensus sequence that are less computationally expensive than conventional methods and that do not require alignment to a reference sequence.

SUMMARY OF THE INVENTION

The invention generally is directed to the area of nucleic acid sequencing, in particular methods, systems and methods for detecting genetic mutations from obtained sequence reads. Systems and methods of the present invention provide for the de novo or assisted assembly of a local graph from a plurality of sequence reads by aligning the sequence reads to one another and to the local graph. The local graph can then be used to perform variant calls with respect to a reference sequence.

A computer-implemented method of identifying a genomic mutation includes, by a processor coupled to a memory area, obtaining a plurality of nucleotide sequence reads mapping to a genomic region of interest with at least one sequence read including at least one mutation, creating in computer memory a directed graph from the plurality of nucleotide sequence reads, and performing variant calls using the created directed graph with a variant being indicative of a mutation. Creation of the directed graph includes the processor: (i) aligning a first sequence read of the plurality of nucleotide sequence reads to a second sequence read of said plurality and producing an alignment indicator; (ii) defining at least one node of the directed graph as a function of the produced alignment indicator, each defined node representing a nucleotide sequence portion; and (iii) successively, for each remaining sequence read after the first and second sequence reads in the obtained plurality of nucleotide sequence reads, aligning the remaining sequence read against the then defined directed graph in computer memory and producing a respective alignment indicator. The produced respective alignment indicator indicates a match to an existing node of the directed graph or extends the directed graph by lengthening a node with additional nucleotide sequences and/or by adding new nodes to incorporate new sequence variations. After the successive aligning of the remaining sequence reads, the resulting, created directed graph represents and describes at least part of the genomic region of interest in detail and, thus, serves as a local assembly of the sequence reads. The directed graph can be a directed acyclic graph (DAG).

The obtained plurality of nucleotide sequence reads can be initially positioned with respect to a reference sequence. Further, the obtained plurality of nucleotide sequence reads can be sorted based on the positioning of the reads with respect to the reference sequence, such that the successive aligning of sequence reads can progress in the sorted order. After the initial positioning, variant calling can be performed resulting in a first set of variant calls. The genomic region of interest can be determined, at least in part, by the first set of variant calls.

An initial positioning with respect to a reference sequence can also assist with rescuing unmapped sequence reads. For example, for a paired-end sequence read, an unmapped sequence read of the pair can be assigned a position based on (i) a position of the other sequence read of the pair, and (ii) an insert size defined as a function of total length of the initially positioned sequence reads. Alternatively, or in addition, the created directed graph can be incorporated into a reference sequence and the plurality of sequence reads can be positioned or re-positioned to the updated reference sequence, thereby rescuing unmapped and/or misaligned sequence reads.

Creating the directed graph can further include aligning the first sequence read to a reference sequence prior to the alignment of the second sequence read to the first sequence read. The reference sequence can be a linear or graph reference genome. Also, the aligning of the first sequence read to the second sequence read can account for gaps between the first and second reads. The aligning of the sequence reads can employ, for example, a Smith-Waterman technique, a Graph-Smith-Waterman technique, or a graph-aware optimal alignment algorithm. The produced alignment indicator can be a Compact Idiosyncratic Gapped Alignment Report (CIGAR) string. Other alignment methods and alignment indicators are suitable.

Defining nodes of the directed graph as a function of the alignment indicator can include the following steps: (i) if the alignment indicator indicates the first and second sequence reads are identical, defining a single node in the directed graph, the single node representing the corresponding identical nucleotide sequence of the first and second sequence reads; (ii) if the alignment indicator indicates the first and second sequence reads are overlapping, defining a single node in the directed graph representing the corresponding overlapping nucleotide sequences of the first and second sequence reads and any nonoverlapping tails of the first and second sequence reads; and, (iii) if the alignment indicator indicates the first and second sequence reads are a variation of each other, defining in the directed graph respective single nodes representing sequence portions in common and respective alternative nodes representing variations.

The created directed graph can be pruned to remove low-confidence nodes to improve variant calling. For example, nodes represented by a low number of mapped sequence reads or low quality sequence reads can be omitted from the graph. Performing variant calls with respect to the resultant created directed graph can include the following steps: transforming at least one path through the directed graph into a contiguous nucleotide sequence by concatenating the nucleotide sequences of or corresponding to the nodes forming the path; aligning the contiguous nucleotide sequence with a reference sequence; and, identifying any differences between the aligned contiguous nucleotide sequence and the reference sequence as a variant.

A computer system for use in identifying a genetic mutation can include a data source providing data representative of a plurality of nucleotide sequence reads mapping to a genomic region of interest and a processor communicatively coupled to the data source. The processor can be configured to create in computer memory a directed graph from the plurality of nucleotide sequence reads of the data source and perform variant calls using the created directed graph. The creation of a directed graph by the processor includes: (i) aligning a first sequence read of the plurality of nucleotide sequence reads to a second sequence read of said plurality and producing an alignment indicator; (ii) defining at least one node of the directed graph as a function of the produced alignment indicator, the defined node representing a nucleotide sequence portion; and, (iii) iteratively, for each remaining sequence read in the plurality after the first and second sequence reads, aligning the remaining sequence read against the then defined directed graph and producing a respective alignment indicator that indicates a match to an existing node of the directed acyclic graph or that extends the directed graph by lengthening a node with additional nucleotide sequences and/or by adding new nodes to incorporate new sequence portions or variations.

A computer program product includes a non-transitory computer readable medium and an executable program stored on the non-transitory computer readable medium. The program when executed by a processor identifies a genetic mutation by: accessing data representative of a plurality of nucleotide sequence reads mapping to a genomic region of interest, creating in computer memory a directed graph from the plurality of nucleotide sequence reads, and performing variant calls using the created directed acyclic graph. The creation of a directed graph by the processor includes: (i) aligning a first sequence read of the plurality of nucleotide sequence reads to a second sequence read of said plurality and producing an alignment indicator; (ii) defining at least one node of the directed graph as a function of the produced alignment indicator, the defined node representing a nucleotide sequence portion; and, (iii) iteratively, for each remaining sequence read in the plurality after the first and second sequence reads, aligning the remaining sequence read against the then defined directed graph and producing a respective alignment indicator that indicates a match to an existing node of the directed graph or that extends the directed graph by lengthening a node with additional nucleotide sequences and/or by adding new nodes to incorporate new sequence portions or variations.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2A illustrates a deletion. FIG. 2B illustrates a single nucleotide polymorphism (SNP). FIG. 2C illustrates a single nucleotide insertion. FIG. 2D illustrates a multiple nucleotide insertion. FIG. 2E illustrates a multiple nucleotide variation.

FIG. 6A illustrates an example of a directed acyclic graph represented by vertices and edges, in which nucleotide sequences are associated with the edges. FIG. 6B illustrates an example of a directed acyclic graph in which the nucleotide sequences are associated with the nodes.

DETAILED DESCRIPTION OF THE INVENTION

Definitions

Figure 1A:
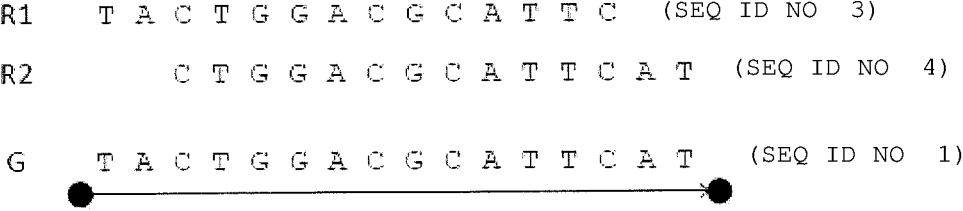
FIG. 1A illustrates the creation of an edge of a directed acyclic graph from the alignment of first and second nucleotide sequence reads having an overlapping sequence portion in accordance with an embodiment of the present invention.

Unless defined otherwise, all technical and scientific terms used herein have the same meaning as commonly understood by one of ordinary skill in the art to which this invention pertains.

As used herein, the singular forms "a", "an," and "the" include plural unless the context clearly dictates otherwise.

A "directed graph" refers to a graph having a topological ordering. A directed graph can be defined by a set of nodes and edges, such that each edge is directed from one node to another. A directed graph can be, for example, a directed acyclic graph or a directed cyclic graph. In certain examples, a directed graph may include only one node and/or edge. Nucleotide sequences can be associated with either the nodes or the edges of a directed graph.

A "directed acyclic graph" or "DAG" refers to a directed graph having no cyclic paths. In embodiments of the present invention, a directed graph can be acyclic when, for example, it represents nucleotide sequences and variations thereof in the 5' to 3' direction.

A "node" refers to an ordered tuple that includes a string (e.g., a set of nucleotide bases), a set of parent nodes, and, optionally, a position. Each node can represent a nucleotide sequence portion (e.g., a section of a conserved sequence, a gene, a nucleic acid, or a single nucleotide, and so forth), including a sequence portion that is a variation. Alternatively, a nucleotide sequence portion can be associated with an edge located between nodes of a directed graph rather than the node itself.

The term "variation" refers to a sequence portion that differs from another sequence portion at the same position in a graph (i.e., a DAG). Types of variations represented in the DAG include, for example, insertions, deletions, single nucleotide polymorphisms (SNPs), and multiple nucleotide variations.

A description of example embodiments of the invention follows.

Conventional Alignment and Assembly Approaches

The application of conventional reference-guided alignment algorithms to next-generation sequencing (NGS) reads is often imperfect. Reference-guided alignment algorithms assume that there is minimal variation between a sequenced genome and the reference genome. As such, reference-guided alignment algorithms can work well for identifying minor variations between the reference sequence and the acquired sequence reads, such as single nucleotide polymorphisms (SNPs) and short insertions and deletions (i.e., indels). However, sequence reads from genomes significantly diverging from the reference genome often map incompletely or do not map at all to the reference genome, thereby resulting in a high percentage of unaligned sequences. Additionally, even when such sequence reads are mapped to the reference genome, variant calling in divergent regions can yield low quality results.

One approach to addressing the problem of performing variant calls on divergent genomes is to perform local assembly, which involves re-assembling a set of sequence reads in region(s) of the reference deemed to be divergent. Upon identifying a region for local assembly, sequence reads mapped to that region are re-assembled de novo into a linear sequence, which is then aligned and compared against the reference sequence to yield higher quality variant calls.

There exists a variety of techniques for assembling a set of sequence reads. Many reference genomes were primarily assembled using the Overlap-Layout-Consensus (OLC) technique. As many reference genomes were sequenced by Sanger-style sequencing methods, long DNA sequence reads were produced that could be mapped to one another using OLC techniques to form a consensus sequence. However, NGS produces a significantly higher number of sequence reads than Sanger-style sequencing, and the produced sequence reads have different properties than those produced by Sanger-style methods, including relatively short sequence lengths and higher error rates. The high number of sequence reads produced by NGS, combined with their short lengths and high error rates, make OLC infeasible as an assembly technique.

The primary assembly technique for NGS is the de Bruijn graph assembler, which adopts a fundamentally different approach than OLC. With de Bruijn graph assemblers, elements of the graph are organized around k-mers, or "words" of k nucleotides (e.g., short DNA sequences consisting of a fixed number of k bases). Sequence reads are mapped as paths through the de Bruijn graph from one k-mer to the next in a determined order. However, because sequence reads are divided into k-mers, de Bruijn graph assemblers have trouble resolving repetitive regions that are longer than the k-mer length. Other assembly techniques include overlap graphs, in which each sequence read is represented by a single node in the graph. However, overlap graphs are computationally expensive, requiring a run time commensurate with $O(N^2)$, where N is the total length of all of the reads, thus limiting their use for many applications.

Local Assembly with a Graph-Aware Algorithm

The present invention provides for systems and methods of performing local assembly of sequence reads that include de novo or assisted construction of directed graphs representing the genomic region of interest. Local assembly methods of the present invention do not require an initial alignment to a reference sequence, and can thereby obviate the reference bias that traditionally occurs with reference-guided alignments. Additionally, local assembly methods of the present invention are less computationally expensive than other de novo assembly techniques, such as overlap graphs, and resolve the shortcomings of de Bruijn graph assemblers with respect to resolving repetitive regions.

In one embodiment, a method of identifying a genomic mutation includes obtaining a plurality of nucleotide sequence reads mapping to a genomic region of interest and creating a directed acyclic graph (DAG) from the obtained sequence reads. Variant calls using the created DAG can then be performed. The creation of the DAG includes the steps of aligning a first sequence read of the plurality of reads to a second sequence read of the plurality of reads and producing an alignment indicator. The alignment indicator describes properties of the alignment of the sequence read to the DAG, and may include information such as a mapped position, matching bases, mismatching bases, insertions, deletions, and other variations between the sequence read and the DAG. In certain embodiments, the alignment indicator can be, for example, a Compact Idiosyncratic Gapped Alignment Report (CIGAR) string (i.e., as described in the Sequence Alignment/Map Format Specification), an Extended CIGAR Format string, an edit distance between the sequence read and the aligned portion of the DAG, and the like. At least one node of the DAG is then defined as a function of the produced alignment indicator. Each node can represent a nucleotide sequence portion, which can include any number of nucleotide bases. Nucleotide sequence portions can alternatively be associated with an edge of the DAG as opposed to a node of the DAG. The method further includes, successively aligning each remaining sequence read of the plurality against the then-defined DAG, each alignment producing a respective alignment indicator that indicates a match to an existing node, or that extends the DAG by lengthening a node (i.e., extending the nucleotide sequence associated with that node) and/or adding new node(s).

For example, if the alignment indicator in the first alignment indicates that the first and the second sequence reads are identical to each other, then a single node is defined in the DAG that represents the corresponding identical nucleotide sequence of the first and second reads. Similarly, if the alignment indicator of a subsequent alignment indicates that the respective aligned read (e.g., $3^{rd}$, $4^{th}$, $5^{th}$ . . . $n^{th}$ read of the plurality of obtained sequence reads) matches a node or a portion of a node already defined in the DAG (i.e., there are no differences between the sequence read and the aligned portions of the DAG), the DAG remains defined as-is and no nodes are lengthened or added.

Alternatively, if the alignment indicator indicates that a first sequence read and second sequence read are overlapping, a single node is defined in the DAG representing a nucleotide sequence read portion that includes the corresponding overlapping nucleotide sequence of the first and second reads as well as the nonoverlapping tails of the first and/or second reads.

Alternatively, if the alignment indicator indicates that a first sequence read and a second sequence read are a variation of each other, the DAG is redefined and extended to include single nodes representing sequence portions in common, as well as alternative nodes representing variants.

Figure 1B:
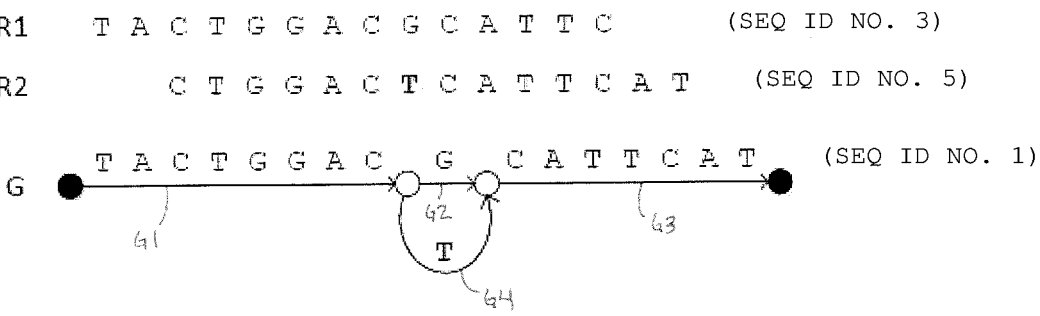
FIG. 1B illustrates the addition of an edge to a directed acyclic graph from an alignment of first and second nucleotide sequence reads having a variation in accordance with an embodiment of the present invention.
Figure 6A:
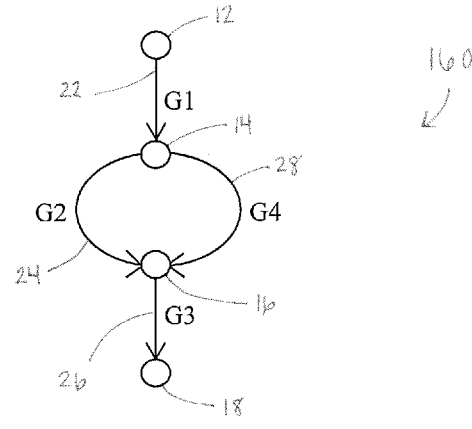
FIGS. 6A and 6B are illustrations of directed acyclic graphs generated by embodiments of performing local assembly.
Figure 6B:
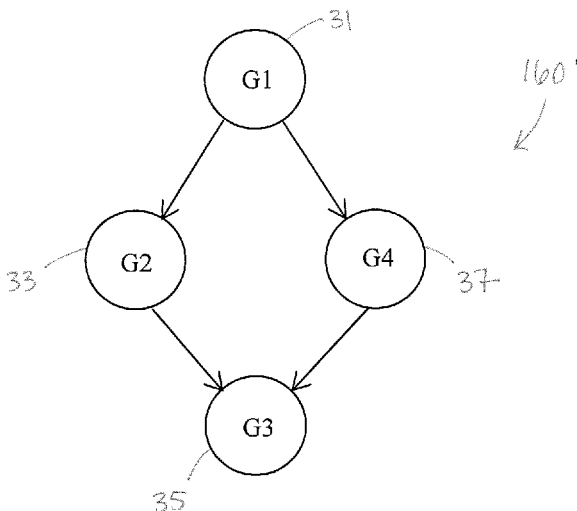

FIGS. 1A-B illustrate the creation of a DAG where sequence reads are overlapping (FIG. 1A) and where sequence reads include a variation (FIG. 1B), with nucleotide sequences associated with edges of the graph, as opposed to nodes. As shown in FIG. 1A, if the alignment indicator indicates that a first sequence read R1 and a second sequence read R2 are overlapping, a single edge is defined in the DAG that represents the nucleotide sequence read portion G. As shown in FIG. 6B, if the alignment indicator indicates that the reads R1 and R2 include a mismatch, the sequence read portion G is redefined and extended to include single edges representing sequence read portions in common G1 and G3, and alternative nodes representing variants G2 and G4.

The invention includes methods for detecting genetic mutations. The methods described herein can be useful in the detection of a variety of genetic mutations, represented as different variant types in a DAG. Mutations that can be detected using the methods described herein include, for example, a single nucleotide polymorphism (SNP), an insertion, a deletion, a tandem duplication, and a rearrangement (e.g., an inversion, a translocation), a structural variation, as well as any combination of the foregoing. The genetic mutation can be a germline mutation or a somatic mutation. In certain examples, the mutation is a known mutation. For example, the mutation can be a recurrent mutation that has been associated with one or more cancers, hereditary disorders, or other diseases or conditions.

Figure 2A:
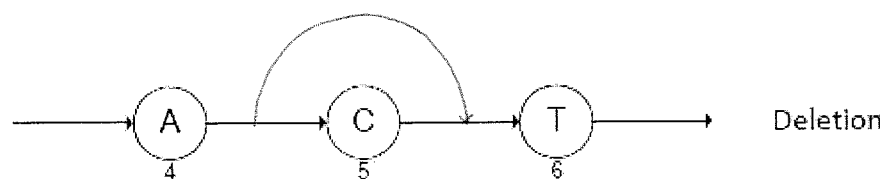
FIGS. 2A-2E illustrate the formation of nodes of a directed acyclic graph for five types of variants.
Figure 2B:
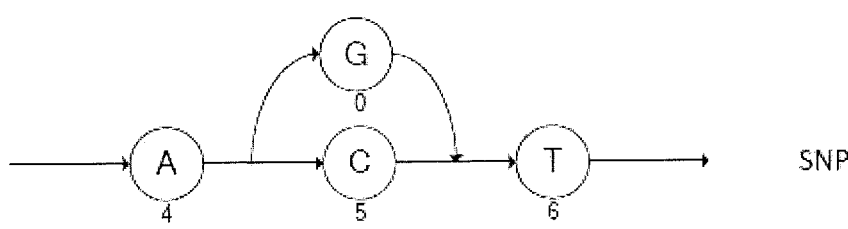
Figure 2C:
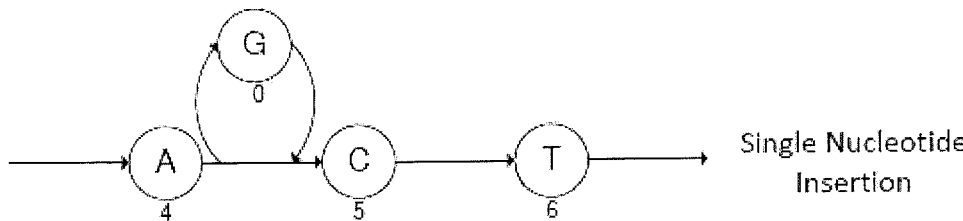
Figure 2D:
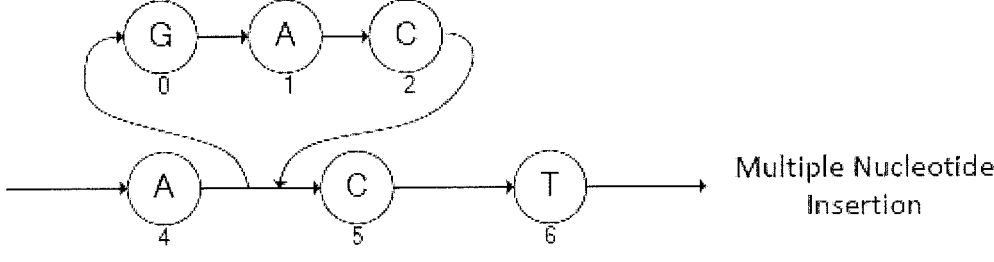
Figure 2E:
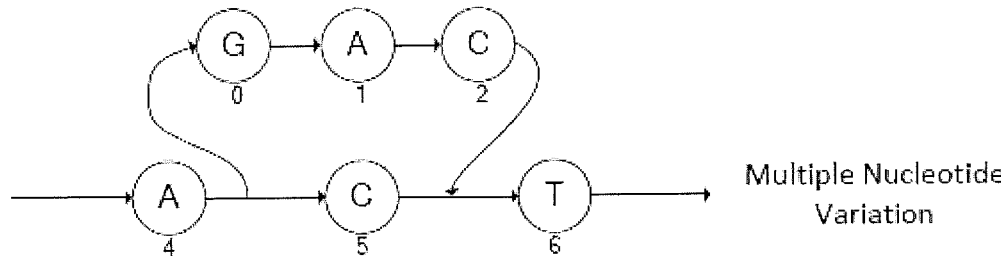

The extension of a DAG to include new nodes representing different variant types is illustrated in FIGS. 2A-2E, including, for example a deletion (FIG. 2A), a single nucleotide polymorphism (SNP) (FIG. 2B), single nucleotide insertion (FIG. 2C), a multiple nucleotide insertion (FIG. 2D), and a multiple nucleotide variation (FIG. 2E). That is, in FIG. 2A, one set of nodes in the DAG represents (as a function of an alignment indicator of a sequence read) the nucleotide sequence "ACT," while another set represents (as a function of a respective alignment indicator of another sequence read) the deletion variant of the nucleotide sequence "AT." The alignment indicator may have been produced based on an initial alignment of a sequence read to another sequence read, or based on an alignment of a sequence read to the DAG as then defined.

In FIG. 2B, there are the nodes in the DAG that represent (as a function of an alignment indicator of the sequence read) the nucleotide sequence "ACT," while another node is added to represent (as a function of a respective alignment indicator of another sequence read) the SNP variant "AGT." In FIG. 2C, added to the node in the DAG that represents the nucleotide sequence "ACT" is the node that represents a single nucleotide insertion thereof, i.e., the nucleotide sequence "AGCT," as a function of an alignment indicator of a succeeding sequence read. As illustrated in FIGS. 2A-2E, each nucleotide has an associated position along a branch, as indicated by the numbers appearing beneath the nodes. In each of FIGS. 2B and 2C, the nucleotide "G" has a position of "0" as it is the first in its branch. Nodes preceding "A" (position 4) and succeeding "T" (position 6) are not shown.

FIG. 2D illustrates the nodes in the DAG that represent the nucleotide sequence "ACT" as described previously, and illustrates the addition of nodes that represent a multiple nucleotide insertion, i.e., the nucleotide sequence "AGACCT." These later nodes are added to the DAG as a function of an alignment indicator of a succeeding sequence read. In FIG. 2E, the nodes in the DAG representing the nucleotide sequence "ACT" have an associated set of nodes that represent a multiple nucleotide variation, i.e., the nucleotide sequence "AGACT," as a function of an alignment indicator of a succeeding sequence read.

Although nucleotide sequences are associated with nodes as described with respect to FIGS. 2A-2E, nucleotide sequences (or any other symbol, such as amino acids) can also be described or defined by edges. For example, shown in FIG. 6A is a DAG 160 having four nodes or vertices 12, 14, 16, 18 and four edges 22, 24, 26, 28. DAG 160 represents the sequence portions, including the variation, illustrated in FIG. 1B. For example, a sequence fragment is read along a line (i.e., edge 22) extending between vertices 12 and 14. Edge 22 represents sequence read portion G1 of FIG. 1B (i.e., "TACTGGAC"). Edge 24 between vertices 14 and 16 represents the sequence read portion G2 (i.e., "G") while edge 28, also located between vertices 14 and 16, represents the SNP sequence variation G4 (i.e., "T"). Lastly, edge 26, located between vertices 16 and 18, represents sequence read portion G3 (i.e., "CAATTCAT"). The illustrated DAG 160, being acyclic and directed, has edges that form a path through G1, G2, and G3 (i.e., representing nucleotide sequence "TACTGGACGCATTCAT" (SEQ ID NO:1)), or a path through G1, G4, and G3 (i.e., representing nucleotide sequence "TACTGGACTCATTCAT" (SEQ ID NO:2)), as indicated by the arrows in FIG. 6A.

The DAG 160 of FIG. 6A can be compared with DAG 160' of FIG. 6B, which represents the same nucleotide sequence portions represented in DAG 160 as nodes instead of as edges. DAG 160' includes four nodes 31, 33, 35, 37. Here, node 31 represents the sequence read portion G1 (i.e., "TACTGGAC"), node 33 represents the sequence read portion G2 (i.e., "G"), node 35 represents the sequence portion G3 (i.e., "CATTCAT"), and node 37 represents the SNP sequence variation G3 (i.e., "T"). The lines or edges connecting the nodes have respective associated directions. As such, similar to DAG 160, paths can be formed through DAG 160' through G1, G2, and G3 (i.e., representing nucleotide sequence "TACTGGACGCATTCAT" (SEQ ID NO:1)), or through G1, G4, and G3 (i.e., representing nucleotide sequence "TACTGGACTCATTCAT" (SEQ ID NO:2)).

The alignment of the first and second sequence reads to each other to form initial node(s) or edge(s) of a DAG, as well as the respective alignments of subsequent sequence reads to the then-defined DAG, can be performed with a graph-aware alignment algorithm, such as, for example, the graph-aware Smith-Waterman algorithm described in U.S. Pat. Pub. No. 2015/0057946, the entire contents of which are incorporated herein by reference. Such graph-aware algorithms can perform alignment of sequence reads to each other and to a DAG by providing for a "look back" type of analysis. A general description of a "look back" type of analysis (for different purposes), is found in, for example, the Smith-Waterman technique (*J Mol Biol,* 147(1):195-197, 1980) and the Gotoh-Smith-Waterman technique (*J Mol Biol,* 162(3), 705-708, 1982). In contrast to the linear methods presented in Smith-Waterman and Gotoh-Smith-Waterman, graph aware algorithms can conduct a "look back" analysis in a multi-dimensional space, considering scores for a plurality of previous nodes, to identify the optimum alignment across a plurality of possible paths of the graph. The alignment indicators produced from such analysis (e.g., CIGAR strings, or edit distance), can then be used to sequentially build a local graph (e.g., a DAG) that represents a divergent region of a sequenced genome in high detail.

While DAGs are shown and described with respect to FIGS. 1A-1B, 2A-2E and 6A-6B, in certain embodiments, graphs created in accordance with the present disclosure may include cycles, and thus would be directed graphs as opposed to directed acyclic graphs.

In some embodiments of the invention, the plurality of nucleotide sequence reads are initially positioned with respect to a reference sequence and sorted according to their mapped position with respect to the reference sequence. The reference sequence to which the sequence reads are aligned can be a linear reference genome or a graph reference genome. For a paired-end sequence read that is unmapped to the reference genome, a position can be assigned to one of the reads of the pair based on the position of the other read of the pair and an insert size that can be inferred from the expected length of the original DNA molecule that generated the pair of sequence reads. In embodiments where nucleotide sequence reads are initially positioned with respect to a reference sequence, an assisted local assembly, as opposed to a de novo local assembly, can then be performed.

Performing an initial positioning step with respect to a reference genome can enable an optional, initial variant calling step to be performed on the mapped sequence reads, thereby yielding a first set of variant calls.

While an initial positioning step is not required in the formation of a DAG, it can assist with identifying a genomic region of interest for local assembly. For example, regions selected for local assembly can be those in which the sequence reads significantly diverge from the reference genome. Significant divergence from the reference genome can be determined by indicia including the following: a relatively large number of aligned sequence reads having a low mapping rate or low mapping quality with respect to the reference genome; overall low coverage of sequence reads in a region in the reference genome; a relatively large number of SNPs near one another (e.g., more than 5 SNPs within a window of 20 bases); the presence of more than one type of variation or allele reported at near or overlapping positions (e.g., both an insertion and a SNP); and the presence of several breakpoints (e.g., mismatches at either 5' or 3' ends of several aligned sequence reads, or the presence of many soft-clipped reads). An identified region for local assembly can include any number of base pairs, for example, tens of base pairs, hundreds of base pairs, or thousands of base pairs.

An initial variant calling step can also assist with identifying a region for local assembly, by, for example, enabling detection of a large number of SNPs near one another or other indicia of significant divergence from the reference genome.

In another embodiment of the present invention, successive aligning of the sequence reads occurs in the order in which the reads are sorted with respect to the reference genome. For example, the first and second sequence reads that are aligned to each other to construct a DAG can be the initial two sequence reads appearing in the sorted order of the reads with respect to the reference genome. In this way, an assisted local assembly can be performed in which the DAG is created using position information from the initial reference alignment, such that the sequence reads successively aligned to the DAG are presented in a pre-sorted (and preferably, overlapping) order. This feature can greatly improve the quality of the resulting DAG and local assembly.

The plurality of nucleotide sequence reads that are being graphed can include paired sequences, unpaired sequences, or a combination thereof. Nucleotide sequence reads correspond to sequences of contiguous nucleotides in a nucleic acid molecule that is being analyzed for the presence of a genetic mutation. The nucleotide sequence can be known to have a mutation, suspected of having a mutation, or be tested for a mutation without knowledge or suspicion as to whether a mutation is present. The nucleic acid molecule can be genomic DNA, cDNA or RNA. In a particular embodiment, the nucleic acid molecule is human genomic DNA.

The nucleic acid molecule can be isolated from a biological source (e.g., a human) employing routine techniques. Biological sources of nucleic acid molecules include nucleic acid molecules extracted from cells, tissues, bodily fluids, and organs. For example, the biological source can be a tissue biopsy (e.g., a tumor biopsy), or a bodily fluid (e.g., blood, bone marrow, plasma, serum, spinal fluid, lymph fluid, tears, saliva, mucus, sputum, urine, fecal matter, semen, and amniotic fluid).

In some embodiments of the invention, the target nucleotide sequences being analyzed are obtained from the products of one or more nucleic acid amplification reactions. One of ordinary skill in the art would understand that the products of such reactions are referred to as amplicons. A variety of nucleic acid amplification reactions are known in the art. In one embodiment, a polymerase chain reaction (PCR) is used to amplify target nucleic acid molecules. Examples of polymerase chain reactions include multiplex polymerase chain reactions and single-plex polymerase chain reactions. Typically, the nucleotide sequences will be obtained with the aid of a sequencer instrument, such as, for example, a Next Generation Sequencer (NGS) sequencer. Sequencing technologies and instruments are known in the art and include, for example, MiSeq® (Illumina, San Diego, CA), Ion Torrent® (Life Technologies, Carlsbad, CA), 454® (454 Life Sciences, Roche, Branford, CT), SOLID® (Applied Biosystems, Thermo Fisher Scientific, Foster City, CA), tSMS™ (Helicos BioSciences, Cambridge, MA), SMRT® (Pacific Biosciences, Menlo Park, CA), and chemFET techniques.

In general, a nucleotide sequence read that is being analyzed using a method described herein will have a length of about 50 to about 500 nucleotides. For example, a nucleotide sequence read can have a length of about 50, about 100, about 150, about 200, about 250, about 300, about 350, about 400, about 450, or about 500 nucleotides. In some embodiments, sequence reads for alignment include at least 50 base pairs (e.g., 50 base pairs, 100 base pairs, 200 base pairs, 500 base pairs). In further embodiments, longer sequence reads (e.g., 500 base pairs or more, 1,000 base pairs or more, 5,000 base pairs or more, and 10,000 base pairs or more) can be required for resolving repetitive regions of the sequenced genome as well as improving alignment of sequence reads to regions of the graph where there exists a gap in coverage. For example, certain "long read" next-generation sequencing technologies such as PacBio® Single Molecule, Real-Time (SMRT) Sequencing can generate sequence reads that range from 10,000 to 60,000 base pairs.

As sequence reads obtained by NGS are inherently noisy, several spurious variations can be included and represented in the defined DAG. In some embodiments, low-confidence nodes (e.g., nodes that are weakly supported by the sequencing reads) may be pruned, or removed, from the DAG. For example, nodes representing a low number of mapped sequence reads (e.g. 5 or fewer sequence reads, or a relatively small number of reads as compared to the average coverage depth of the obtained reads) and/or nodes represented by low quality sequence reads (e.g., positions having a low average per-base quality, such as a Phred score of, for example, less than 10, less than 5, or 0) can be pruned from the DAG.

In a further embodiment of the present invention, a created DAG can be incorporated into a reference sequence, and the plurality of sequence reads can be positioned or re-positioned with respect to the updated reference sequence incorporating the DAG. As the genomic region selected for local assembly can be highly divergent, several sequence reads may be unmapped or mapped incorrectly. A re-positioning of the entire set of sequence reads to an updated reference can rescue unmapped or misaligned sequence reads. The incorporation of the created DAG into the reference sequence can be performed several times during the alignment process. For example, several iterations of local graph assembly and re-positioning with respect to an updated reference sequence can be performed. After each iteration the positioning of unmapped or misaligned sequence reads and subsequent alignments of such reads produces an improved DAG that more accurately represents the region of interest. This process is particularly helpful for closing gaps in a local assembly. In certain embodiments, one may insert only a single contiguous sequence from the DAG back into the reference sequence. For example, a concatenated set of sequences from a path through the DAG having the highest associated coverage, quality scores, or other characteristics can be selected and incorporated to form an updated reference.

Once a DAG (e.g., a DAG 160 including vertices and edges or a DAG 160' including nodes, FIGS. 6A-6B) has been created, variant calling can be performed. The number of paths that can be taken through the DAG is dependent upon the number of nodes representing variations in the graph. Generally, the number of paths available is equal to $2^N$, where N represents the number of alternative nodes that are included in the DAG. To perform a variant call, at least one path through the created DAG can be transformed into a contiguous nucleotide sequence (e.g., a contig) by concatenating the nucleotide sequences of the nodes forming the path. The contiguous nucleotide sequence can then be aligned with a reference sequence and any differences between the aligned contiguous sequence and the reference sequence can be identified as a variant. This process can be repeated for each possible path through the created DAG.

While a DAG may include several paths, for a diploid sample, only two paths through the DAG are true representations of the nucleotide sequences corresponding to each haplotype or chromosome. Given the large number of paths that may be available through a DAG, variant calling can be performed on any number of possible paths. For example, every possible path can be considered and candidate events can be determined from all possible paths. Alternatively, a reduced number of paths can be considered. For example, paths can be ranked by quality criteria, such as a number of associated sequence reads, a number of mapped sequence reads, and the like, and only the paths most likely to be an accurate representation of the sequenced genome may be considered. In addition, phasing information of events can be considered to select paths having sequence reads in which several events are present. For example, a fifty base pair sequence read having two SNPs supports a premise that those SNPs are located on the same chromosome.

As methods of the present invention include constructing a DAG de novo, larger and more complex events can be identified during variant calling than would occur with a reference-guided alignment. Methods for identifying and evaluating candidate events are known in the art and include, for example, the PairHMM algorithm (see Richard Durbin, Sean R. Eddy, Anders Krogh, and Graeme Mitchison, Biological Sequence Analysis: Probabilistic Models of Proteins and Nucleic Acids, Cambridge University Press, 1999), and the Genome Analysis Toolkit (GATK, Broad Institute, Cambridge, MA).

Local assembly methods of the present invention have several advantages over other assembly methods. For example, the creation of an overlap graph requires significant computational resources and time to complete, as a comparison of every sequence read to every other sequence read must be performed. In contrast, methods according to the present invention compare only successive sequence reads to a local graph (e.g., a then-defined DAG), reducing the total number of comparisons that are to be performed.

While methods exist to reduce the number of comparisons required in generating an overlap graph, such as, for example FM indices, such methods increase the complexity of the assembly process. Other assembly methods, such as de Bruijn graph assemblers, are less computationally expensive than overlap graphs. However, the performance of de Bruijn graph assemblers is poor with respect to resolving repetitive regions of a sequenced genome as each sequence read is segmented into a plurality of smaller k-mers. In contrast, local assembly methods of the present invention are simpler to execute while providing improved accuracy and the ability to resolve repetitive regions.

As methods of the present invention begin by aligning sequence reads directly to one another in a sorted manner, alignment of the sequence reads occurs with only minimal reference-bias. However, local graphs of the present invention can be constructed based on an alignment of the first sequence read to the reference sequence, instead of the alignment of the second sequence read to the first sequence read. As such, the basis for the local graph can be the reference itself. This may be preferable in situations in which there is low coverage in the region selected for local assembly, and, thus, a lack of overlapping reads that is sufficient for generating a high quality DAG.

In another embodiment, an alignment indicator may be rejected if it indicates substantial variation between a successive sequence read and a local graph (or a first sequence read). For example, if the local graph does not yet include the region including the sequence read (i.e., there are no overlapping portions), the resulting alignment will be of low quality and suggest that there are many variations present (e.g., more than 25% of the aligned bases are mismatches). In such cases, that sequence read and the associated alignment indicator may be "skipped" and not integrated into the local graph. In certain embodiments, the skipped sequence read may be reconsidered; for example, one could attempt to re-align that sequence read to the local graph once all of the other reads have been processed.

Figure 3:
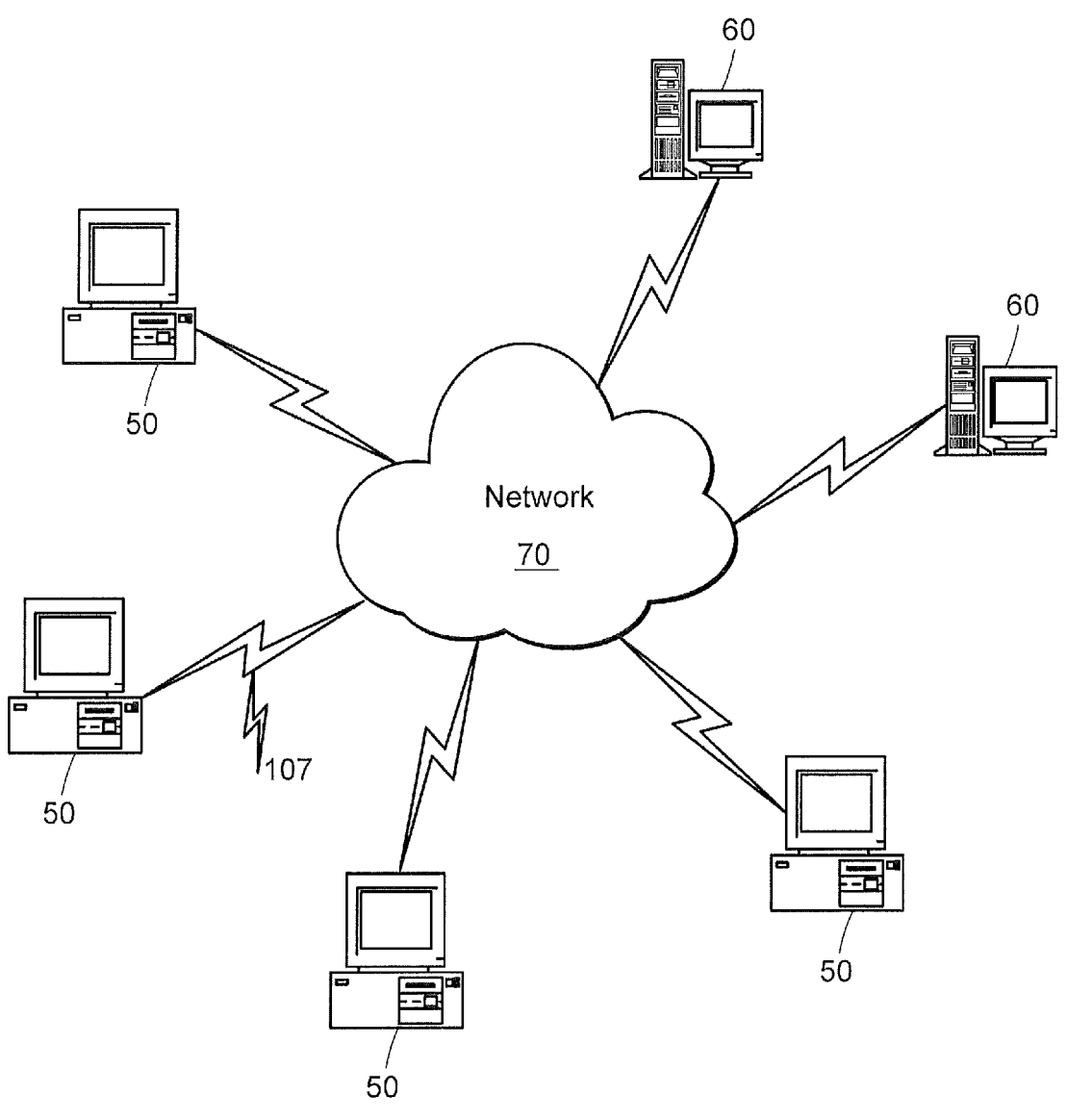
FIG. 3 is a schematic view of a computer network environment in which embodiments of the present invention may be deployed.

FIG. 3 illustrates a computer network or similar digital processing environment in which embodiments of the present invention may be implemented. Client computer(s)/devices/exercise apparatuses 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, cloud computing servers or service, Local area or Wide area networks, and gateways that currently use respective protocols (TCP/IP, Bluetooth, etc.) to communicate with one another. Other electronic device/computer network architectures are suitable.

Figure 4:
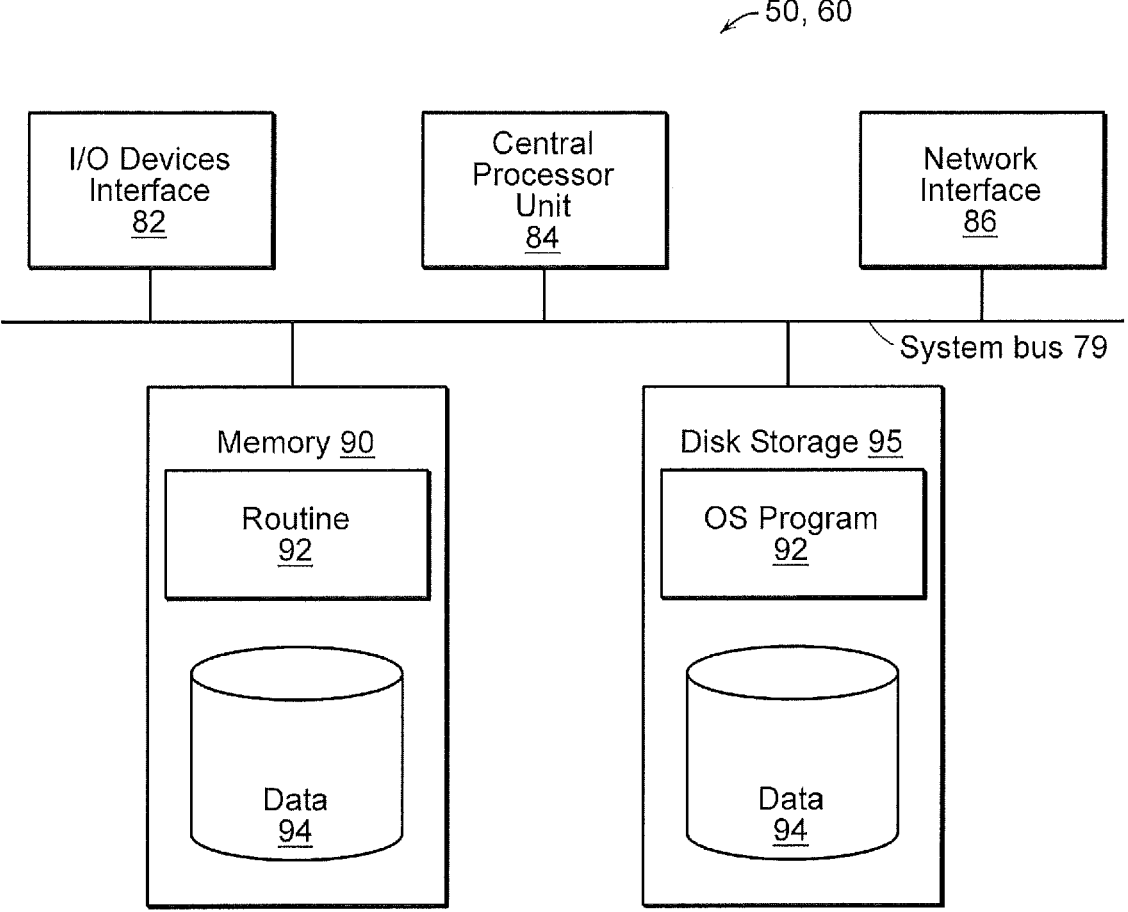
FIG. 4 is a block diagram of computer nodes or devices in the computer network of FIG. 3.

FIG. 4 is a diagram of the internal structure of a computer (e.g., client processor/device 50 or server computers 60) in the computer network of FIG. 3. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 3). Memory 90 provides volatile storage for computer software instructions 92 and data 94 used to implement embodiments of the present invention (e.g., processor routines and code for creating a directed acyclic graph (DAG) as a function of computed alignment indices and aligning sequence reads against the DAG being developed, as described herein). Disk storage 95 provides nonvolatile storage for computer software instructions 92 and data 94 used to implement an embodiment of the present invention. Central processor unit 84 is also attached to system bus 79 and provides for the execution of computer instructions.

Figure 5:
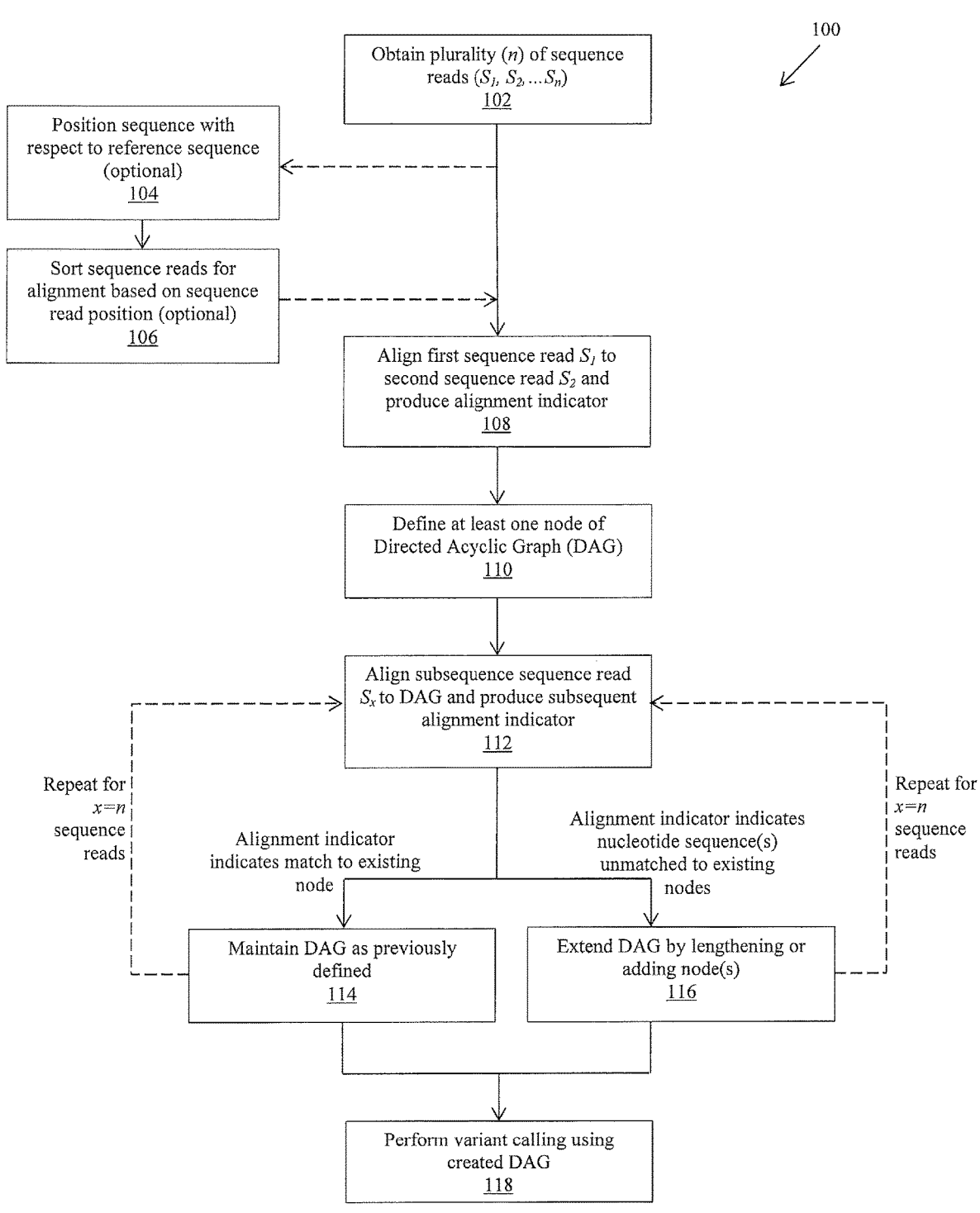
FIG. 5 is a flow diagram of a computer processor operation 100 in embodiments of the present invention.

In particular, embodiments of the present invention execute the processor routine 100 illustrated in FIG. 5. Initially, a plurality of sequence reads ($S_1$, $S_2$, . . . $S_n$) are obtained at step 102. The plurality of sequence reads can optionally be positioned with respect to a reference sequence at step 104, followed by sorting at step 106, such that the plurality of sequence reads are subsequently aligned in a sorted order based upon their determined position. The performance of steps 104 and 106 can increase the probability that the reads, as sorted, will overlap with one another, thus resulting in better quality alignments. At step 108, a first sequence read $S_1$ is aligned to a second sequence read $S_2$, and an alignment indicator is produced. Based upon the produced alignment indicator, at least one node of a DAG is defined at step 110. For example, if $S_1$ and $S_2$ are identical or if $S_1$ and $S_2$ include an overlapping sequence read portion, a single node is produced representing the sequence portion in common, as well as any tails of $S_1$ and/or $S_2$, if present. The DAG as defined at step 110 would thus include a single node. As an alternative example, if $S_1$ and $S_2$ are variations of each other, at least two nodes of a DAG are defined at step 110. For example, if $S_2$ includes a SNP (as illustrated in FIG. 1B), nodes representing the sequence portions in common and nodes representing the variation are defined. The DAG as defined at step 110 would thus include at least four nodes.

Subsequent sequence reads of the plurality of sequence reads are then aligned to the DAG at step 112, and subsequent alignment indicators are produced. If an alignment indicator indicates a match of a subsequent sequence read to an existing node or set of nodes of the DAG (i.e., there are no variations between the sequence read and the DAG that should be newly incorporated), the DAG is maintained at step 114. Alternatively, if an alignment indicator indicates that a subsequent sequence read includes nucleotide sequence(s) unmatched to existing nodes, the DAG is extended at step 116 by the lengthening of existing node(s) or the addition of new node(s). Steps 112-116 represent an iterative processes by which each subsequent sequence read (i.e., $S_3$, $S_4$, . . . $S_n$) is aligned to a then-defined DAG. Following creation of the DAG, variant calling is performed at step 118.

In one embodiment, the processor routines 92 and data 94 are a computer program product (generally referenced 92), including a non-transitory computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternative embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, other mediums and the like.

In other embodiments, the computer program product 92 provides Software as a Service (SaaS) or similar operating platform.

Alternative embodiments can include or employ clusters of computers, parallel processors, or other forms of parallel processing, effectively leading to improved performance, for example, of generating a computational model. Given the foregoing description, one of ordinary skill in the art understands that different portions of processor routine 100 and different iterations operating on respective sequence reads may be executed in parallel on such computer clusters or parallel processors.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of identifying a genomic mutation, the method comprising:

by a processor coupled to a memory area, the memory area comprising a plurality of nucleotide sequence reads mapping to a genomic region of interest:

creating in computer memory a directed graph from the plurality of nucleotide sequence reads by:

(i) aligning a first sequence read of the plurality of nucleotide sequence reads to a second sequence read of said plurality and producing an alignment indicator;

(ii) defining at least one node of the directed graph as a function of the produced alignment indicator, each defined node representing a nucleotide sequence portion;

(iii) successively, for each remaining sequence read after the first and second sequence reads, aligning the remaining sequence read against the then defined directed graph and producing a respective alignment indicator that indicates a match to an existing node of the directed graph or that extends the directed graph by lengthening a node with additional nucleotide sequences, by adding new nodes to incorporate new sequence variations, or a combination thereof, the created directed graph providing a local assembly of the sequence reads;

performing variant calls with the created directed graph and a reference genome, the performing variant calls including detecting a variant, represented in a node of the directed graph, with respect to the reference genome; and providing an output identifying a genomic mutation based on the detected variant.

2. The method of claim 1, further comprising initially positioning the plurality of nucleotide sequence reads with respect to a reference sequence and sorting the plurality of nucleotide sequence reads based on the positioning of said sequence reads with respect to the reference sequence; and wherein the successive aligning progresses in sorted order of the nucleotide sequence reads.

3. The method of claim 1, wherein creating the directed graph includes aligning the first sequence read to the reference sequence prior to the alignment of the second sequence read to the first sequence read.

4. The method of claim 2, wherein the reference sequence is a linear or graph reference genome.

5. The method of claim 2, further comprising performing variant calls at the initial positioning, resulting in a first set of variant calls.

6. The method of claim 5, wherein the genomic region of interest is determined by the first set of variant calls.

7. The method of claim 2, the sorting further comprising: for a paired-end sequence read that is unmapped to the reference genome, assigning a position to one of the unmapped sequence reads of a pair based on (i) position of the other sequence read of the pair, and (ii) an insert size defined as a function of an inferred length of a DNA molecule that originated the paired-end sequence read.

8. The method of claim 1, wherein the aligning of the first sequence read to the second sequence read accounts for gaps between the first and second sequence reads.

9. The method of claim 1, wherein:

the aligning of sequence reads employs a Smith-Waterman technique, a Graph-Smith-Waterman technique, or a graph-aware optimal alignment algorithm; and the produced alignment indicator is a Compact Idiosyncratic Gapped Alignment Report (CIGAR) string.

10. The method of claim 9, wherein defining the nodes of the directed graph as a function of the produced CIGAR strings includes:

(i) if the CIGAR string indicates the first and second sequence reads are identical, defining a single node in the directed graph, the single node representing the corresponding identical nucleotide sequence of the first and second sequence reads;

(ii) if the CIGAR string indicates the first and second sequence reads are overlapping, defining a single node in the directed graph representing the corresponding overlapping nucleotide sequences of the first and second sequence reads and any nonoverlapping tails of the first and second sequence reads; and (iii) if the CIGAR string indicates the first and second sequence reads are a variation of each other, defining in the directed graph respective single nodes representing sequence portions in common and respective alternative nodes representing variations.

11. The method of claim 1, wherein defining the nodes of the directed graph as a function of the alignment indicator includes:

(i) if the alignment indicator indicates the first and second sequence reads are identical, defining a single node in the directed graph, the single node representing the corresponding identical nucleotide sequence of the first and second sequence reads;

(ii) if the alignment indicator indicates the first and second sequence reads are overlapping, defining a single node in the directed graph representing the corresponding overlapping nucleotide sequences of the first and second sequence reads and any nonoverlapping tails of the first and second sequence reads;

(iii) if the alignment indicator indicates the first and second sequence reads are a variation of each other, defining in the directed graph respective single nodes representing sequence portions in common and respective alternative nodes representing variations.

12. The method of claim 1, further comprising pruning the created directed graph by removing low-confidence nodes, wherein the low-confidence nodes represent a low number of mapped sequence reads or low-quality sequence reads.

13. The method of claim 1, further comprising incorporating the created directed graph into a reference sequence and re-positioning the plurality of sequence reads to the updated reference sequence incorporating the created directed graph, rescuing unmapped and/or misaligned sequence reads.

14. The method of claim 1, wherein performing variant calls includes:

transforming at least one path through the directed graph into a contiguous nucleotide sequence by concatenating the nucleotide sequences of the nodes forming the path, aligning the contiguous nucleotide sequence with a reference sequence, and identifying any differences between the aligned contiguous nucleotide sequence and the reference sequence as a variant.

15. The method of claim 1, wherein the directed graph is a directed acyclic graph.

16. A computer system for use in identifying a genetic mutation, the system comprising:

a data source providing data representative of a plurality of nucleotide sequence reads mapping to a genomic region of interest; and a processor communicatively coupled to the data source, the processor configured to:

create in computer memory a directed graph from the plurality of nucleotide sequence reads by:

(i) aligning a first sequence read of the plurality of nucleotide sequence reads to a second sequence read of said plurality and producing an alignment indicator;

(ii) defining at least one node of the directed graph as a function of the produced alignment indicator, each defined node representing a nucleotide sequence portion;

(iii) iteratively, for each remaining sequence read after the first and second sequence reads, aligning the remaining sequence read against the then defined directed graph and producing a respective alignment indicator that indicates a match to an existing node of the directed graph or that extends the directed graph by lengthening a node with additional nucleotide sequences, by adding new nodes to incorporate new sequence variations, or a combination thereof, the created directed graph providing a local assembly of the sequence reads;

perform variant calls with the created directed graph and a reference genome, the performing variant calls including detecting a variant, represented in a node of the directed graph, with respect to the reference genome; and provide an output identifying a genomic mutation based on the detected variant.

17. The computer system of claim 16, wherein the processor is further configured to initially position the plurality of sequence reads with respect to a reference sequence and sort the plurality of sequence reads based on the position of said sequence reads with respect to the reference sequence, and wherein the iterative aligning iterates in order of the sequence reads resulting from said sort.

18. The computer system of claim 16, wherein the processor is further configured to create the directed graph in computer memory by aligning the first sequence read to a reference sequence prior to the alignment of the second sequence read to the first sequence read.

19. The computer system of claim 17, wherein the reference sequence is a linear or graph reference genome.

20. The computer system of claim 17, wherein the processor is further configured to perform variant calls at the initial positioning, resulting in a first set of variant calls.

21. The computer system of claim 20, wherein the processor is further configured to determine the genomic region of interest by the first set of variant calls.

22. The computer system of claim 17, wherein the processor is further configured to sort the plurality of sequence reads by, for a paired-end sequence read that is unmapped to the reference genome, assigning a position to one of the unmapped sequence reads of a pair based on (i) position of the other sequence read of the pair, and (ii) an insert size defined as a function an inferred length of a DNA molecule that originated the paired-end sequence read.

23. The computer system of claim 16, wherein the wherein the processor is further configured to account for gaps between the first and second sequence reads during the alignment of the first sequence read to the second sequence read.

24. The computer system of claim 16, wherein:
the aligning of sequence reads employs a Smith-Waterman technique, a Graph-Smith-Waterman technique, or a graph-aware optimal alignment algorithm; and
the produced alignment indicator is a Compact Idiosyncratic Gapped Alignment Report (CIGAR) string.

25. The computer system of claim 24, wherein defining the nodes of the directed graph as a function of the produced CIGAR strings includes:
(i) if the CIGAR string indicates the first and second sequence reads are identical, defining a single node in the directed graph, the single node representing the corresponding identical nucleotide sequence of the first and second sequence reads;
(ii) if the CIGAR string indicates the first and second sequence reads are overlapping, defining a single node in the directed graph representing the corresponding overlapping nucleotide sequences of the first and second sequence reads and any nonoverlapping tails of the first and second sequence reads; and
(iii) if the CIGAR string indicates the first and second sequence reads are a variation of each other, defining in the directed graph respective single nodes representing sequence portions in common and respective alternative nodes representing variations.

26. The computer system of claim 16, wherein defining the nodes of the directed graph as a function of the alignment indicator includes:
(i) if the alignment indicator indicates the first and second sequence reads are identical, defining a single node in the directed graph, the single node representing the corresponding identical nucleotide sequence of the first and second sequence reads;
(ii) if the alignment indicator indicates the first and second sequence reads are overlapping, defining a single node in the directed graph representing the corresponding overlapping nucleotide sequences of the first and second sequence reads and any nonoverlapping tails of the first and second sequence reads;
(iii) if the alignment indicator indicates the first and second sequence reads are a variation of each other, defining in the directed graph respective single nodes representing sequence portions in common and respective alternative nodes representing variations.

27. The computer system of claim 16, wherein the processor is further configured to prune the created directed graph by removing low-confidence nodes, wherein the low-confidence nodes represent a low number of mapped sequence reads or low-quality sequence reads.

28. The computer system of claim 16, wherein the processor is further configured to incorporate the created directed graph into a reference sequence and re-position the plurality of sequence reads to the updated reference sequence incorporating the created directed graph, rescuing unmapped and/or misaligned sequence reads.

29. The computer system of claim 16, wherein the processor is further configured to perform variant calls by:
transforming at least one path through the directed graph into a contiguous nucleotide sequence by concatenating the nucleotide sequences of nodes forming the path,
aligning the contiguous nucleotide sequence with a reference sequence, and
identifying any differences between the aligned contiguous nucleotide sequence and the reference sequence as a variant.

30. The computer system of claim 16, wherein the directed graph is a directed acyclic graph.

31. A computer program product comprising:
a non-transitory computer readable medium; and
an executable program stored on the non-transitory computer readable medium, the program being for identifying a genetic mutation by:
accessing data representative of a plurality of nucleotide sequence reads mapping to a genomic region of interest;
creating in computer memory a directed graph from the plurality of nucleotide sequence reads, including:
(i) aligning a first sequence read of the plurality of nucleotide sequence reads to a second sequence read of said plurality and producing an alignment indicator;
(ii) defining at least one node of the directed graph as a function of the produced alignment indicator, the defined node representing a nucleotide sequence portion;
(iii) iteratively, for each remaining sequence read after the first and second sequence reads, aligning the remaining sequence read against the then defined directed graph and producing a respective alignment indicator that indicates a match to an existing node of the directed graph or that extends the directed graph by lengthening a node with additional nucleotide sequences, by adding new nodes to incorporate new sequence portions or variations, or a combination thereof, the created directed graph providing a local assembly of the sequence reads; and performing variant calls with the created directed graph and a reference genome, the performing variant calls including detecting a variant, represented in a node of the directed graph, with respect to the reference genome; and providing an output identifying a genomic mutation based on the detected variant.

* * * * *